US012763201B2

(12) United States Patent
Wang et al.

(10) Patent No.: US 12,763,201 B2
(45) Date of Patent: Oct. 13, 2026

(54) MEDICAL DEVICE UNDERCARRIAGE

(71) Applicant: Siemens Shanghai Medical Equipment Ltd., Shanghai (CN)

(72) Inventors: Li Wang, Shanghai (CN); Min Li, Shanghai (CN); Yin Jie Xiang, Shanghai (CN)

(73) Assignee: Siemens Shanghai Medical Equipment Ltd., Shanghai (CN)

( * ) Notice: Subject to any disclaimer, the term of this patent is extended or adjusted under 35 U.S.C. 154(b) by 381 days.

(21) Appl. No.: 18/575,401

(22) PCT Filed: Sep. 2, 2021

(86) PCT No.: PCT/CN2021/116210
§ 371 (c)(1),
(2) Date: Dec. 29, 2023

(87) PCT Pub. No.: WO2023/272930
PCT Pub. Date: Jan. 5, 2023

(65) Prior Publication Data
US 2024/0321443 A1 Sep. 26, 2024

(30) Foreign Application Priority Data
Jun. 29, 2021 (CN) ......................... 202110729994.0

(51) Int. Cl.
*A61B 6/00* (2024.01)
*G16H 40/63* (2018.01)

(52) U.S. Cl.
CPC .................................. *G16H 40/63* (2018.01)

(58) Field of Classification Search
CPC ........ G16H 40/63; A61B 6/4405; A61B 6/54; A61B 6/547; A61B 6/032; A61B 6/0487
See application file for complete search history.

(56) References Cited

U.S. PATENT DOCUMENTS

2011/0093172 A1 4/2011 Chen et al.
2015/0375778 A1 12/2015 Pastor et al.
2017/0215825 A1 8/2017 Johnson et al.
2017/0215826 A1 8/2017 Johnson et al.
2019/0099140 A1 4/2019 Garlow et al.
2020/0016927 A1 * 1/2020 Dietrich ................ A61B 6/035
(Continued)

FOREIGN PATENT DOCUMENTS

CN 1918014 A 2/2007
CN 101221447 A 7/2008
(Continued)

OTHER PUBLICATIONS

Mar. 11, 2022 (PCT) International Search Report and Written Opinion—App. PCT/CN2021/116210.

*Primary Examiner* — Uzma Alam
*Assistant Examiner* — Mamadou Faye
(74) *Attorney, Agent, or Firm* — Banner & Witcoff, Ltd.

(57) ABSTRACT

A medical device undercarriage including a pair of front wheels, a pair of rear wheels, a first position sensitive detector located between the pair of front wheels, a second position sensitive detector located between the pair of rear wheels, and a controller. The controller is operable to calculate a gear ratio of the rear wheels according to a position of the first position sensitive detector and a position of the second position sensitive detector.

6 Claims, 2 Drawing Sheets

(56) References Cited

U.S. PATENT DOCUMENTS

| | | | |
|---|---|---|---|
| 2020/0121267 | A1 | 4/2020 | Deutschmann |
| 2020/0245966 | A1 | 8/2020 | I et al. |

FOREIGN PATENT DOCUMENTS

| | | | |
|---|---|---|---|
| CN | 102042395 | A | 5/2011 |
| CN | 108601569 | A | 9/2018 |
| CN | 209280580 | U | 8/2019 |
| CN | 110406593 | A | 11/2019 |
| CN | 111717204 | A | 9/2020 |
| JP | 2001347423 | A | 12/2001 |

* cited by examiner

MEDICAL DEVICE UNDERCARRIAGE

TECHNICAL FIELD

The present disclosure relates to a medical device system, and in particular, to a medical device undercarriage.

BACKGROUND

During CT scanning, a patient is usually moved by a patient support system (examination table). However, in some special cases, for example, if the patient is under surgery or has an open wound, the patient cannot be moved, and CT scanning is performed by moving a gantry. This requires a movable gantry undercarriage that can carry and transport the gantry. With this undercarriage, the gantry can be transported outside the scanning room and used in several rooms.

Motion precision is very important for mobile CT and is directly related to the image quality of scanning. However, the motion precision of the mobile CT is affected by a variety of factors, including ground flatness and installation precision of a mechanical structure.

SUMMARY

In view of this, the present disclosure provides a medical device undercarriage and a medical device system.

According to a first aspect of the present disclosure, a medical device undercarriage is provided, including a pair of front wheels, a pair of rear wheels, a first position sensitive detector located between the pair of front wheels, a second position sensitive detector located between the pair of rear wheels, and a controller; and the controller calculates a gear ratio of the rear wheels according to a position of the first position sensitive detector and a position of the second position sensitive detector.

In an embodiment, if a position deviation of the first position sensitive detector is $E_p(n)$, the controller calculates $E_p(n)$ according to the following formula:

$$E_p(n) = K_{pp} * \frac{E_p(n-1)}{dt} + K_{pi} * \frac{\sum_{i=0}^{N} E_p(n-i)}{N * dt} + K_{pd} * \frac{\sum_{i=0}^{N} [E_p(n-i) - 2E_p(n-i-1) + E_p(n-i-2)}{N * dt}$$

where N is a positive integer, and dt is a sampling interval, $K_{pp}$, $K_{pi}$, and $K_{pd}$ are respectively proportional integral differential coefficients of related positions.

In an embodiment, if the position of the first position sensitive detector is $P_1$, the position of the second position sensitive detector is $P_2$, and an angle deviation of the second position sensitive detector is $E_a(n)$, the controller calculates $E_a(n)$ according to the following formula:

$$E_a(n) = \frac{d(P_2 - P_1)}{1000} + E_p(n)$$

where $d(P_2-P_1)$ is a position difference between the first position sensitive detector and the second position sensitive detector.

In an embodiment, if the gear ratio of the rear wheels is GR, the controller calculates GR according to the following formula:

$$GR = 1 + K_{ap} * [E_a(n) - E_a(n-1)] + K_{ai} * E_a(n) * dt + K_{ad} * \frac{E_a(n) - 2E_a(n-1) + E_a(n-2)}{dt}$$

where $K_{ap}$, $K_{ai}$, and $K_{ad}$ are respectively proportional integral differential coefficients of related angles.

In an embodiment, $N \in [25, 1000]$.

In an embodiment, the front wheel includes a mobile encoder, a mobile motor, and a mobile drive, and the rear wheel includes a steering encoder, a steering motor, and a steering drive.

According to a second aspect of the present disclosure, a medical device system is provided, including a medical device and the medical device undercarriage described above, where the medical device is disposed on the medical device undercarriage, and the controller sends the gear ratio of the rear wheels to the medical device.

For the medical device undercarriage and system of the present disclosure, no track is required to control motion, and no absolutely flat ground is required. The medical device undercarriage and system can be used on a relatively flat ground, have low costs, and are slightly environment-dependent.

BRIEF DESCRIPTION OF THE DRAWINGS

To enable a person of ordinary skill in the art to understand the foregoing and other features and advantages of the present disclosure more clearly, exemplary embodiments according to the present disclosure are described in detail below with reference to the accompanying drawings. In the accompanying drawings.

Figure 1:
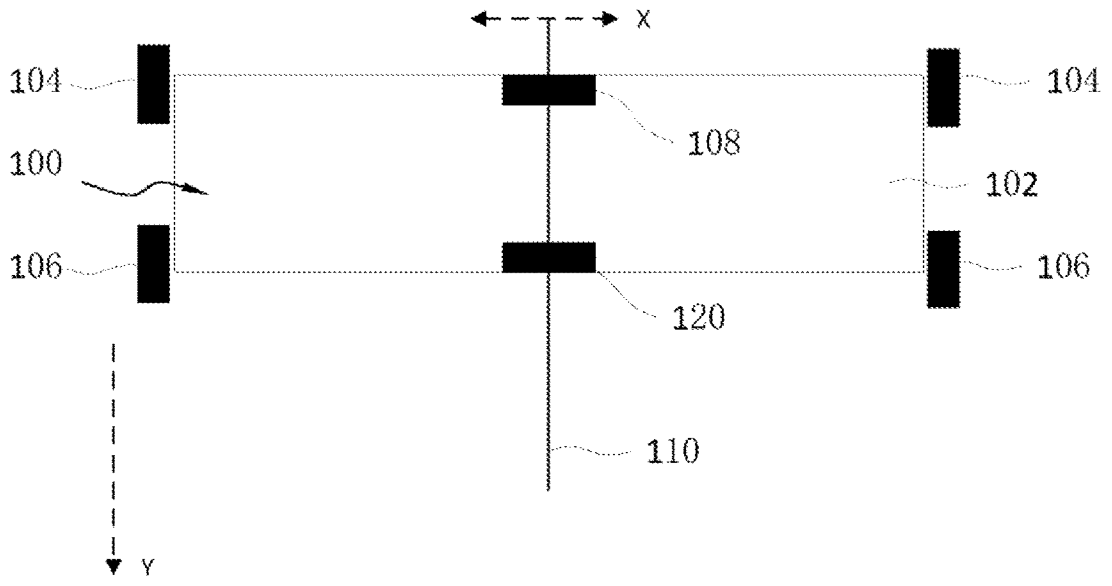
FIG. 1 is a schematic structural diagram of a medical device undercarriage according to an embodiment of the present disclosure.

In the accompanying drawings, the reference numerals used are as follows:

| | |
|---|---|
| 100 | Medical device undercarriage |
| 101 | Steering motor |
| 102 | Undercarriage plate |
| 103 | Steering encoder |
| 104 | Rear wheel |
| 105 | Steering drive |
| 106 | Front wheel |
| 107 | Mobile motor |
| 108 | Second position sensitive detector |
| 109 | Mobile encoder |
| 110 | Laser beam |
| 111 | Mobile drive |
| 112 | Position deviation |
| 113 | Controller |
| 114 | Angle deviation |
| 116 | Path planning |
| 117 | Medical device |
| 118 | Origin |
| 120 | First position sensitive detector |

DETAILED DESCRIPTION

To make the objective, technical solutions, and advantages of the present disclosure clearer, the present disclosure is further described in detail below by using embodiments.

Figure 2:
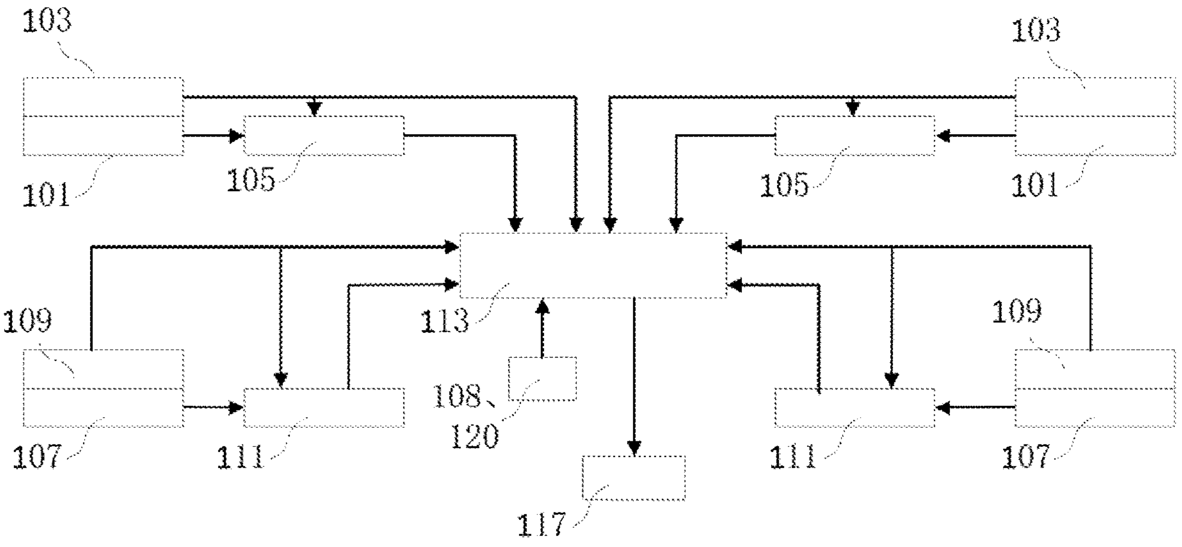
FIG. 2 is a functional block diagram of a medical device undercarriage according to an embodiment of the present disclosure.

FIG. 1 is a schematic structural diagram of a medical device undercarriage 100 according to an embodiment of the present disclosure. FIG. 2 is a functional block diagram of the medical device undercarriage 100 according to an embodiment of the present disclosure. Ideally, the medical device undercarriage 100 will travel in a Y direction, but in fact, it will be offset in an X direction. Motion inertia of a gantry is very large, and a back gap exists in a mobile mechanism, so it is difficult to measure a static error. To reduce the impact on scanning and reconstruction, a deviation in the X direction should be within 2 mm.

As shown in FIG. 1 and FIG. 2, the medical device undercarriage 100 includes an undercarriage plate 102, a pair of front wheels 106, a pair of rear wheels 104, a first position sensitive detector 120 located between the pair of front wheels 106, a second position sensitive detector 108 located between the pair of rear wheels 104, and a controller 113. The first position sensitive detector 120 and the second position sensitive detector 108 emit a laser beam 110.

As shown in FIG. 2, the front wheel 106 includes a mobile encoder 109, a mobile motor 107, and a mobile drive 111, and the rear wheel 104 includes a steering encoder 103, a steering motor 101, and a steering drive 105. The first position sensitive detector 120 and the second position sensitive detector 108 send their position information to the controller 113. The controller 113 calculates a gear ratio of the rear wheels 104 according to a position of the first position sensitive detector 120 and a position of the second position sensitive detector 108. A medical device 117 may be disposed on the medical device undercarriage 100, and the controller 113 may send the gear ratio to the medical device 117.

Offsets of the two positions on the undercarriage 100 relative to the traveling direction may be obtained from the first position sensitive detector 120 and the second position sensitive detector 108. The position of the first position sensitive detector 120 is $P_1$, the position of the second position sensitive detector 108 is $P_2$, the position $P_1$ of the first position sensitive detector 120 is a position error, and $P_2-P_1$ is an angle error.

Figure 3:
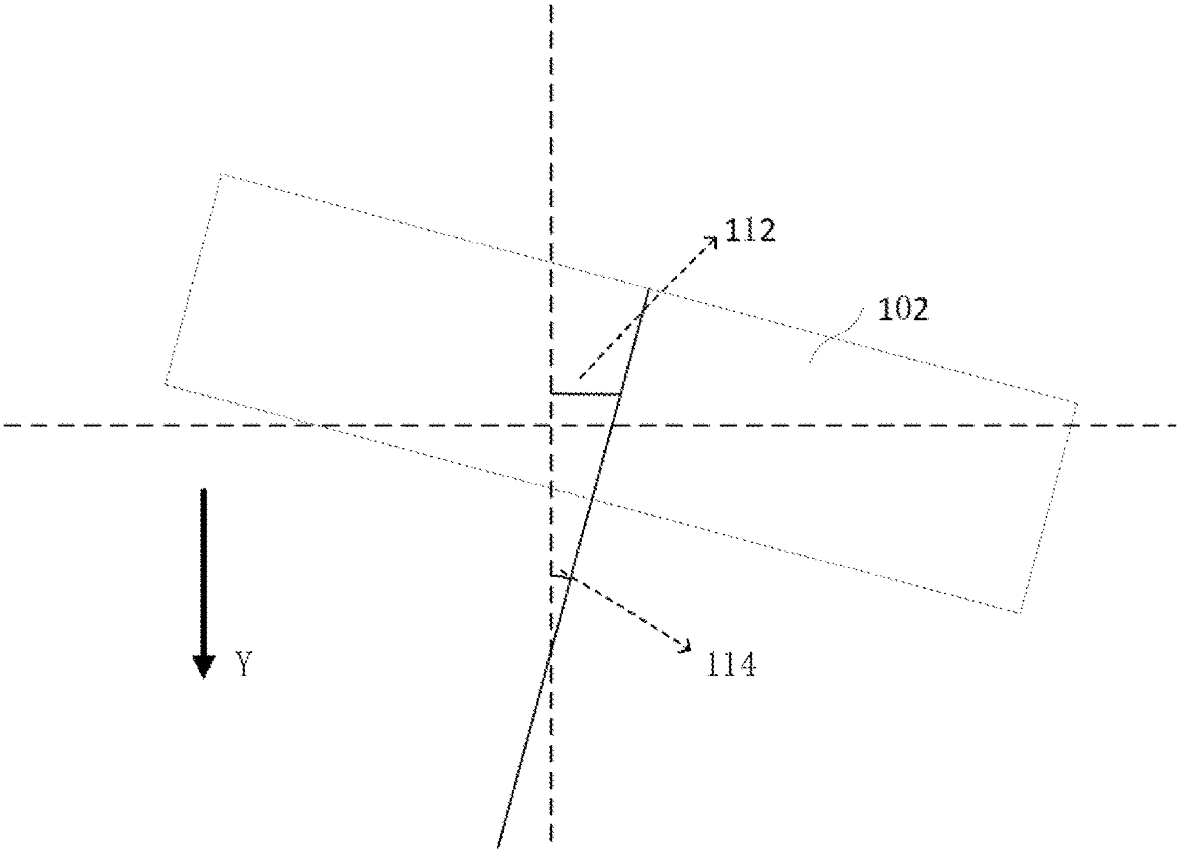
FIG. 3 is a schematic diagram of position and angle deviations of a medical device undercarriage according to an embodiment of the present disclosure.

FIG. 3 is a schematic diagram of a position deviation 112 and an angle deviation 114 of a medical device undercarriage 100 according to an embodiment of the present disclosure.

First, to reduce the position error of $P_1$, the position deviation is used as an input to the first proportional integral differential (PID) loop, and a half-position PID algorithm is used herein. Deviation values of a position sensitive detector at N sampling points are recorded as input deviation values, and N may be a value between 25 and 1000, which can not only increase the reliability of deviation correction but also reduce processor burden.

If a position deviation of the first position sensitive detector 120 is $E_p(n)$, the controller 113 may calculate $E_p(n)$ according to the following formula:

$$E_p(n) = K_{pp} * \frac{E_p(n-1)}{dt} + K_{pi} * \frac{\sum_{i=0}^{N} E_p(n-i)}{N * dt} +$$

-continued $$K_{pd} * \frac{\sum_{i=0}^{N} [E_p(n-i) - 2E_p(n-i-1) + E_p(n-i-2)}{N * dt}$$

where N is a positive integer, and dt is a sampling interval, $K_{pp}$, $K_{pi}$, and $K_{pd}$ are respectively proportional integral differential coefficients of related positions, and may be obtained through test.

Then, the obtained correction deviation is added to the adjustment of the angle deviation so that the adjustment of the angle deviation approaches 0 and reduces the position deviation.

If an angle deviation of the second position sensitive detector 108 is $E_a(n)$, the controller 113 may calculate $E_a(n)$ according to the following formula:

$$E_a(n) = \frac{d(P_2 - P_1)}{1000} + E_p(n)$$

where $d(P_2-P_1)$ is a position difference between the first position sensitive detector 120 and the second position sensitive detector 108. In this embodiment, $d(P_2-P_1)$ is in a unit of micron. Therefore, it needs to be divided by 1000 for unit conversion.

A correction amount obtained after the PID loop is compared with an existing speed difference and further correction is performed. In addition, to increase motion flexibility and smoothness, a rear wheel swivel angle is added, and a deviation angle of the rear wheel is obtained in real time by using a motion center as an origin according to a differential deviation that needs to be corrected.

If the gear ratio of the rear wheels 104 is GR, the controller 113 may calculate GR according to the following formula:

$$GR = 1 + K_{ap} * [E_a(n) - E_a(n-1)] + K_{ai} * E_a(n) * dt + K_{ad} * \frac{E_a(n) - 2E_a(n-1) + E_a(n-2)}{dt}$$

where $K_{ap}$, $K_{ai}$, and $K_{ad}$ are respectively proportional integral differential coefficients of related angles, and may be obtained through test.

Figure 4:
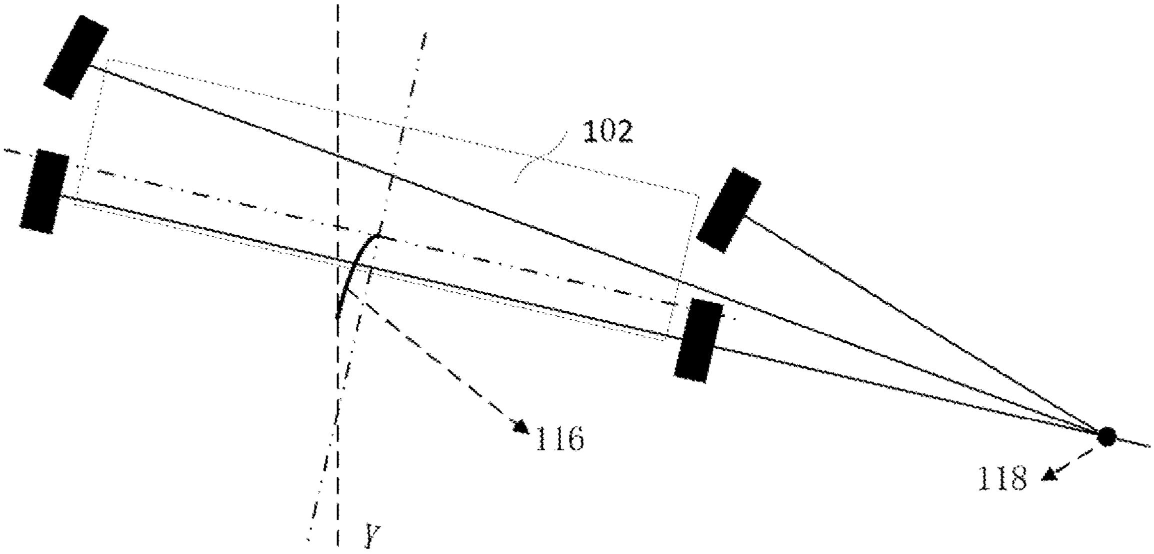
FIG. 4 is a schematic diagram of the motion of a medical device undercarriage according to an embodiment of the present disclosure.

FIG. 4 is a schematic diagram of the motion of a medical device undercarriage 100 according to an embodiment of the present disclosure. The rear wheel 104 is deflected around an origin 118 so that an undercarriage plate 102 has path planning 116, thereby returning to the ideal traveling route Y.

A measurement range of a high-precision position sensitive detector (PSD) is +/−17 mm, and the resolution is 0.01 mm. In this embodiment, a distance between steering wheels (rear wheels) is 2605 mm, and a diameter of the steering wheel is 198 mm. If only traveling wheels (front wheels) are controlled synchronously in real time, a deviation of 5-7 mm will occur when moving by 1000 mm at 100 mm/s. With the controller of this embodiment, the deviation is reduced to 2 mm.

The present disclosure further provides a medical device system, including a medical device 117 and the medical device undercarriage 100. The medical device 117 is disposed on the medical device undercarriage 100. The controller 113 sends the gear ratio of the rear wheels 104 to the medical device 117.

For the medical device undercarriage and system of the present disclosure, no track is required to control motion, and no absolutely flat ground is required. The medical device undercarriage and system can be used on a relatively flat ground, have low costs, and are slightly environment-dependent.

The foregoing descriptions are merely preferred embodiments of the present disclosure but are not intended to limit the present disclosure. Any modification, equivalent replacement, or improvement made within the spirit and principle of the present disclosure shall fall within the protection scope of the present disclosure.

What is claimed is:

1. A medical device undercarriage, comprising:

a pair of front wheels;

a pair of rear wheels;

a first position sensitive detector located between the pair of front wheels;

a second position sensitive detector located between the pair of rear wheels; and a controller operable to calculate a gear ratio of the rear wheels according to a position of the first position sensitive detector and a position of the second position sensitive detector, wherein if a position deviation of the first position sensitive detector is $E_p(n)$, the controller is operable to calculate $E_p(n)$ according to the following formula:

$$E_p(n) = K_{pp} * \frac{E_p(n-1)}{dt} + K_{pi} * \frac{\sum_{i=0}^{N} E_p(n-i)}{N * dt} + K_{pd} * \frac{\sum_{i=0}^{N} [E_p(n-i) - 2E_p(n-i-1) + E_p(n-i-2)]}{N * dt},$$

wherein N is a positive integer, and dt is a sampling interval, $K_{pp}$, $K_{pi}$, and $K_{pd}$ are respectively proportional integral differential coefficients of related positions.

2. The medical device undercarriage according to claim 1, wherein if the position of the first position sensitive detector is $P_1$, the position of the second position sensitive detector is $P_2$, and an angle deviation of the second position sensitive detector is $E_a(n)$, the controller is operable to calculate $E_a(n)$ according to the following formula:

$$E_a(n) = \frac{d(P_2 - P_1)}{1000} + E_p(n),$$

$d(P_2-P_1)$ representing a position difference between the first position sensitive detector and the second position sensitive detector.

3. The medical device undercarriage according to claim 2, wherein if the gear ratio of the rear wheels is GR, the controller is operable to calculate GR according to the following formula:

$$GR = 1 + K_{ap} * [E_a(n) - E_a(n-1)] + K_{ai} * E_a(n) * dt + K_{ad} * \frac{E_a(n) - 2E_a(n-1) + E_a(n-2)}{dt},$$

wherein $K_{ap}$, $K_{ai}$, and $K_{ad}$ are respectively proportional integral differential coefficients of related angles.

4. The medical device undercarriage according to claim 1, wherein $N \in [25, 1000]$.

5. The medical device undercarriage according to claim 1, wherein the front wheel comprises a mobile encoder, a mobile motor, and a mobile drive, and wherein the rear wheel comprises a steering encoder, a steering motor, and a steering drive.

6. A medical device system, comprising:

a medical device; and the medical device undercarriage according to claim 1, wherein the medical device is disposed on the medical device undercarriage, and the controller is operable to send the gear ratio of the rear wheels to the medical device.

* * * * *